United States Patent [19]
Holt et al.

[11] Patent Number: 5,856,361
[45] Date of Patent: Jan. 5, 1999

[54] PAIN RELIEVER AND METHOD OF USE

[75] Inventors: Stephen D. Holt; Timothy R. Laughlin, both of Little Rock, Ark.

[73] Assignee: Medical Merchandising, Inc., Little Rock, Ark.

[21] Appl. No.: 870,261

[22] Filed: Jun. 6, 1997

Related U.S. Application Data

[63] Continuation-in-part of Ser. No. 635,149, Apr. 23, 1996, abandoned.

[51] Int. Cl.$^6$ ....................................................... A61K 31/16
[52] U.S. Cl. ............................ 514/627; 514/825; 514/887
[58] Field of Search ..................................... 514/627, 825, 514/887

[56] References Cited

U.S. PATENT DOCUMENTS 4,939,149  7/1990  Blumberg et al. ...................... 514/691

OTHER PUBLICATIONS

Chemical Abstracts AN 1995:778316, Billany et al., Jan. 1995.

Chemical ABstracts AN 1985:32273, JP 59181209 A2, "Topical pastes containing rosemary extracts . . . ", Mar. 30, 1985.

Chemical Abstracts AN 1985:172679, JP 60013710, "Thermal poultices containing camphor and ginger . . . ", Jan. 24, 1985.

*Primary Examiner*—Keith D. MacMillan
*Attorney, Agent, or Firm*—Wendy K. Buskop; Chamberlain, Hrdlicka et al

[57] ABSTRACT

A composition containing capsaicin together with another ingredient to neutralize the discomfort resulting from the application of capsaicin to the skin can be used to treat many types of discomforts, including musculo-skeletal pain, neuralgia and neurpathies, without the discomfort normally associated with the topical application of capsaicin.

52 Claims, No Drawings

PAIN RELIEVER AND METHOD OF USE

RELATED APPLICATION

This is a continuation-in-part application of U.S. patent application Ser. No. 08/635,149 that was filed on Apr. 23, 1996 now abandoned.

BACKGROUND OF THE INVENTION

In one aspect, this invention relates to a composition of matter useful for treating bodily pains and discomforts. In another aspect, this invention relates to a method for treating bodily pains and discomforts. In yet another aspect, this invention relates to formulating a pain and discomfort reliever.

Arthritis is medically termed as an inflammation of a joint or joints and is one of a number of diseases and disorders of the skeleton and body system. Arthritis arises from many causes, some well-defined, some still unknown, and it is treated in many different ways. There are two common types, the first of which is inflammatory, of which rheumatoid arthritis is the most commonly acknowledged and a non-inflammatory, second type, most commonly represented by degenerative joint disease, or "wear and tear" arthritis. Inflammatory arthritis is a disease not of the joints alone but of the whole bodily system, in particular, the connective tissues of the body. It is an autoimmune disease, where the body's immune system attacks its own host (i.e. itself) and produces inflammation. Degenerative joint disease is a chronic joint disease, often occurring in more elderly people. In both cases many manifestations are similar. The joints, whether singly or in multiples, are affected. The joints may become swollen, warm, deformed, gnarled, and in many instances present grotesque deformities. In many cases it also affects the adjacent muscles and tendons, as well as other connective tissues of the body. The primary disease produces symptomatic swelling, pain and stiffness.

Various new and old drugs have been developed for the treatment of arthritis, anywhere from non-steroidal anti-inflammatory drugs to cortisone. Many of these systemic drugs have dangerous side effects. Their dosage must be carefully prescribed and administered under controlled conditions and circumstances to avoid unpleasant and dangerous side effects.

Several topical agents (creams, ointments, liniments and the like) have been utilized for the relief of the pains and aches of arthritis and related disorders. Most of these have provided a little, but only temporary, relief to persons suffering from pain. Many combinations of varying ointments, creams, aqueous solutions, liniments and the like for the treatment of arthritis are known. The most efficacious of these contains as its active ingredient the vegetable products derived from the seed and pods of the capsicum plant, commonly known as red pepper. Capsicum-derived topical agents are devised for external application to the affected area of the body by applying to the area adjacent to the muscle, joint, ligament or tendon and then rubbing it into the skin. The active ingredient is capsaicin. With initial as well as continuous use, capsaicin is effective to relieve the aches and pains of various musculo-skeletal disorders, such as arthritis, muscle strains, sprains, tendinitis, bursitis and other soft tissue diseases.

Capsaicin is also effective to relieve the various musculoskeletal pains, itching, neuropathic pains, dysesthesias caused by shingles, post herpetic neuralgia, post mastectomy pain, and peripheral neuropathies. It is further commonly prescribed to reduce the pain of neuropathies produced by diabetes (burning pain, discomfort, often at night) and other diseases that are neuropathic in origin including the discomfort and odd sensations of shingles (post herpetic neuralgia, which can be extremely painful), as well as dysesthesias that can occur with thoracotomies and post surgical scars.

Unfortunately, although capsaicin is often the most effective agent available, the active ingredient is a potent skin irritant, producing a burning, uncomfortable sensation to the skin. Although prescribed frequently, it is used to only a limited extent due to this unpleasant side effect.

The burning side effect has also discouraged the use of capsaicin to treat other types of discomfort, such as pruritus or itching. Pruritus or itching can be caused by many stimuli, such as poison ivy, hemorrhoids, or athlete's foot. The unpleasant side effects of capsaicin have discouraged its use to treat such types of discomfort.

A capsaicin based pain reliever which does not irritate the skin or cause a burning discomfort would be extremely desirable and acceptable to patients and people in general who are experiencing the types of pain or discomfort outlined above.

OBJECTS OF THE INVENTION

It is an object of this invention to provide a capsaicin based pain reliever that does not burn when applied topically.

It is another object of this invention to provide a method for formulating a no-burn capsaicin-based pain reliever that relieves pain and discomfort and in which the capsaicin is fully functional.

It is a further object of this invention to provide a method for treating pain and discomfort with capsaicin that does not burn the skin or mucus membranes.

SUMMARY OF THE INVENTION

In accordance with one aspect of the invention, there is provided a composition comprising a first active ingredient and at least one second active ingredient in a carrier fluid. The first active ingredient comprises capsaicin. The at least one second active ingredient is to reduce the sensation of capsaicin induced skin irritation.

In accordance with another aspect of the invention, there is provided a method for treating a victim of pain or discomfort. The treatment comprises applying the above described composition topically to the skin of the victim near an area affected by the pain or discomfort.

In accordance with a further aspect of the invention, there is provided a method for making a composition useful for topical application to treat pain or discomfort. The method is carried out by mixing a carrier with at least one first active ingredient comprising capsaicin and at least one second active ingredient to reduce capsaicin induced skin irritation to form an aqueous or oil-based solution, or a solid stick applicator or patch, of the at least one first active ingredient and the at least one second active ingredient in the carrier. The aqueous solution preferably has a cream-like viscosity.

DETAILED DESCRIPTION OF THE PREFERRED EMBODIMENTS

Capsaicin is trans-8-methyl-N-vanillyl-5 nonenamide, a naturally occurring alkyl vanillylamide, a type of capsaicinoid. It is found in high concentration in fruit of plants of the Capsicum genus. The chili pepper, red pepper and paprika are all species of Capsicum. Capsicum is the dry powder obtained by grinding up the fruits of these plants. *Capsicum*

*oleoresin* (or capsaicin oleoresin) is the liquid concentrate extracted from the dry powder. Capsaicin, a white crystalline material, is obtained from the liquid concentrate.

The composition of the invention comprises capsaicin as a first active ingredient and at least one second active ingredient is to reduce the sensation of capsaicin induced skin irritation. The ingredients are contained in a carrier.

Generally speaking, the composition will contain in the range of 0.00125% to 1% by weight of capsaicin. However, compositions containing less than 0.00125% by weight of capsaicin will provide a diminishing, but still therapeutic, effect. Even trace concentrations of capsaicin (such as 0.00001% by weight) will provide a minute therapeutic effect. Compositions containing more than 1% by weight of capsaicin will also provide a therapeutic effect, except that the burning side effect will increase in proportion to the increase percentage of capsaicin. Compositions containing 5%, or more, by weight of capsaicin could be used, but the burning sensation is considered intense. For these reasons, compositions containing in the range of 0.025% to 0.25% by weight of capsaicin are preferred because they are narrowly encompassed within current FDA guidelines. However, the FDA guidelines were developed at a time when there was not an effective method for relieving the discomfort generated by capsaicin. The present invention increases the amount of capsaicin that can be administered comfortably. Generally speaking, a sufficient amount of the at least one second active ingredient is mixed with the carrier to reduce the skin irritation and pain which is caused by the capsaicin.

Preferably, a fluid carrier is water-based and forms an aqueous solution containing the ingredients. An oil-based carrier solution containing the ingredients is an alternative to the aqueous carrier solution. Either aqueous or oil-based solutions further contain thickening agents to provide the composition with the viscosity of a liniment, cream, ointment, gel, or the like. Suitable thickening agents are well known.

Alternative embodiments of the present invention can also use a solid carrier containing the active ingredients. This enables the alternative embodiment to be applied via the familiar stick applicator or a patch. The solid carrier further contains thickening agents to provide the composition with the consistency of wax or paraffin.

The at least one second active ingredient can be of various functionalities. The second active ingredient can be selected from the group consisting of at least one binding agent for binding capsaicin and at least one topical analgesic agent for analgesthetizing against pain caused by the effects of capsaicin.

It is preferred that the second active ingredient comprise a plant extract. For example, a selection from the group consisting of a nettle extract, a yarrow extract, a coltsfoot extract, a birch extract, a rosemary extract, a horsetail extract, a ginger extract, a chamomile extract, a comfrey extract, a lavender extract, and a bergamot extract is expected to be beneficial.

While the preferred embodiment of the present invention includes all of the above-mentioned extracts, individual extracts can be excluded to achieve diminished, though therapeutic, results. The order of effectiveness of the various extracts is listed below:

1. lavender extract
2. bergamot extract
3. rosemary extract
4. ginger extract
5. chamomile extract
6. comfrey extract
7. coltsfoot extract
8. nettle extract
9. yarro extract
10. birch extract
11. horsetail extract For example, an alternate second active ingredient that eliminated only the horsetail extract would be more effective than an alternate second active ingredient that eliminated only the lavender extract. Furthermore, the concentrations of the various extracts can be varied or eliminated to achieve enhanced or diminished effectiveness of the alternate second active ingredients.

Nettle extract can be obtained from the leaves of *Urtica dioca*. It is a medium green-yellow liquid which is soluble in water, has a characteristic odor, a specific gravity in the range of 1.02 to 1.05 at 25 degrees C, a pH in the range of 4.0 to 7.0 at 25 degrees C, and a refractive index in the range of 1.3860 to 1.3950 at 25 degrees C.

Yarrow extract can be obtained from the flowers of *Achillea millefolium*. It is a light to medium amber liquid which is soluble in water, has a characteristic odor, a specific gravity in the range of 1.02 to 1.05 at 25 degrees C, a pH in the range of 4.0 to 6.5 at 25 degrees C, and a refractive index in the range of 1.3860 to 1.3950 at 25 degrees C.

Coltsfoot extract can be obtained from the leaves of *Tussilago farfara*. It is a light to medium amber liquid which is soluble in water, has a characteristic odor, a specific gravity in the range of 1.02 to 1.05 at 25 degrees C, a pH in the range of 4.0 to 6.5 at 25 degrees C, and a refractive index in the range of 1.3860 to 1.3950 at 25 degrees C.

Birch extract can be obtained from the leaves of *Betula alba*. It is a light to medium amber liquid which is soluble in water, has a characteristic odor, a specific gravity in the range of 1.02 to 1.05 at 25 degrees C, a pH in the range of 4.0 to 6.5 at 25 degrees C, and a refractive index in the range of 1.3860 to 1.3950 at 25 degrees C.

Rosemary extract can be obtained from the leaves of *Rosmarinus officinalls*. It is a light to medium amber liquid which is soluble in water, has a characteristic odor, a specific gravity in the range of 1.02 to 1.05 at 25 degrees C, a pH in the range of 4.0 to 5.5 at 25 degrees C, and a refractive index in the range of 1.3860 to 1.3950 at 25 degrees C.

Horsetail extract can be obtained from the whole plant of *Equiseturn hyemale*. It is a light to medium amber liquid which is soluble in water, has a characteristic odor, a specific gravity in the range of 1.02 to 1.05 at 25 degrees C, a pH in the range of 4.0 to 5.5 at 25 degrees C, and a refractive index in the range of 1.3860 to 1.3950 at 25 degrees C.

Ginger extract can be obtained from the roots of *Zingiber officinale*. It is a light to medium amber liquid which is soluble in water, has a characteristic odor, a specific gravity in the range of 1.02 to 1.05 at 25 degrees C, a pH in the range of 4.0 to 6.5 at 25 degrees C, and a refractive index in the range of 1.3860 to 1.3950 at 25 degrees C.

Chamomile extract can be obtained from the flowers of *Matricaria chamomilla*. It is a light to medium amber liquid which is soluble in water, has a characteristic odor, a specific gravity in the range of 1.02 to 1.05 at 25 degrees C, a pH in the range of 4.0 to 6.5 at 25 degrees C, and a refractive index in the range of 1.3860 to 1.3950 at 25 degrees C.

Comfrey extract can be obtained from the leaves of *Symphyturn officinale*. It is a light to medium amber liquid which is soluble in water, has a characteristic odor, a specific gravity in the range of 1.02 to 1.05 at 25 degrees C, a pH in the range of 4.0 to 6.5 at 25 degrees C, and a refractive index in the range of 1.3860 to 1.3950 at 25 degrees C.

Lavender extract can be obtained from the flowers of *Lavandula officinalis*. It is a light to medium amber liquid which is soluble in water, has a characteristic odor, a specific gravity in the range of 1.02 to 1.05 at 25 degrees C, a pH in the range of 4.0 to 6.5 at 25 degrees C, and a refractive index in the range of 1.3860 to 1.3950 at 25 degrees C.

Bergamot extract can be obtained from the flowers of *Monarda didyma*. It is a light to medium amber liquid which is soluble in water, has a characteristic odor, a specific gravity in the range of 1.02 to 1.05 at 25 degrees C, a pH in the range of 4.0 to 6.5 at 25 degrees C, and a refractive index in the range of 1.3860 to 1.3950 at 25 degrees C.

The plant extracts can be used in the form of propylene glycol-water solutions of the indicated materials.

The composition of the invention will often also contain a polyol such as a polyol selected from the group consisting of propylene glycol, glycerine, polyethylene glycol, butylene glycol, and triethanolamine. Other ingredients such as inositol, methyl paraben, propyl paraben, carbomer 940 and DL-panthenol may be present if desired.

In the method of the invention, a victim of pain or discomfort is treated by applying the above described composition topically to the skin of the victim near an area affected by the pain or discomfort. The types of pain or discomfort to which the invention may be applied include those discussed in the background of the invention. Generally speaking, the inventive composition, preferably in ointment or cream form, is applied to the selected area, such as a joint, and rubbed in. The amount applied is not critical. Generally, it should be applied in an amount which is sufficient to wet the area of application. Usually, the amount used will be in the range of from about 0.3 to about 3 ccs.

For the treatment of pruritus or itching, the application of the composition can be repeated as required to control the discomfort. When the preferred composition of the invention is applied, it provides near immediate relief from the itching caused by poison ivy or hemorrhoids, without a burning sensation. The relief lasts for several hours. It is surprising that a capsaicin based composition would be useful for the treatment of such discomfort. Capsaicin, as part of the present invention, has been shown to be effective in relieving: 1) musculo-skeletal pains (e.g., arthritis, tendinitis, bursitis, myalgias, arthralgias, strains, sprains, ligamentous disorders, etc.); 2) peripheral neuropathy and other dysesthesias (e.g., diabetic peripheral neuropathy with numb burning feet); 3) post herpetic neuralgia (painful syndrome after shingles and other viral illnesses); 4) post mastectomy/post thoracotomy scar pain; and 5) pruritus and itching of all forms, whether contact dermatitis (e.g., poison ivy), immunological (e.g., angioedema that occurs with systemic lupus erythematosus or urticaria that occurs with various allergic reactions), drug reactions (e.g., sulfa, penicillin, etc.), insect bites, systemic metabolic disorders (e.g., pruritus that occurs with renal dialysis), mechanical maceration (e.g., hemorrhoids) and idiopathic pruritus.

For best results in the treatment of arthritis, the treatment should be repeated several times per day, such as in the range of 2 to 8 times per day, preferably 3–5 times per day, and continued for several days. Surprisingly, most patients do not experience the burning discomfort heretofore known as a very common side effect of topical capsaicin application.

The forgoing is a description of the composition and method of use of an embodiment of the invention. The scope of the invention is considered to include the described embodiment together with others obvious to those skilled in the art.

EXAMPLE

A composition made in accordance with one embodiment of the invention contains the following ingredients.

| Ingredient | wt. % |
| --- | --- |
| deionized water | 81.00 |
| propylene glycol | 5.00 |
| glycerine | 3.00 |
| polyethylene glycol | 1.00 |
| butylene glycol | 1.00 |
| triethanolamine | .60 |
| inositol | .20 |
| methyl paraben | .10 |
| propyl paraben | .10 |
| carbomer 940 | .30 |
| DL-Panthenol | 1.00 |
| nettle extract | .50 |
| yarrow extract | .50 |
| coltsfoot extract | .50 |
| birch extract | .50 |
| rosemary extract | .50 |
| horsetail extract | .50 |
| ginger extract | .50 |
| chamomile extract | .50 |
| comfrey extract | .50 |
| lavender extract | .50 |
| bergamot extract | .50 |
| capsaicin | .025 |

What is claimed is:

1. A composition comprising:
    a carrier;
    a first active ingredient comprising capsaicin; and
    at least one second active ingredient that functions as an analgesic to reduce capsaicin induced skin irritation, wherein the at least one second active ingredient is selected from the group consisting of a polyol, a nettle extract, a yarrow extract, a coltsfoot extract, a birch extract, a rosemary extract, a horsetail extract, a ginger extract, a chamomile extract, a comfrey extract, a lavender extract, and a bergamot extract.

2. A composition as in claim 1 comprising in the range of 0.0001% to 0.025% by weight of capsaicin.

3. A composition as in claim 1 comprising in the range of 0.025% to 0.25% by weight of capsaicin.

4. A composition as in claim 3 wherein the carrier is an aqueous fluid.

5. A composition as in claim 4 further comprising a thickening agent to provide the composition with the consistency selected from the group consisting of liniment, cream, gel, and ointment.

6. A composition as in claim 5 comprising at least one binding agent for binding capsaicin as a second active ingredient.

7. A composition as in claim 3 wherein the polyol is selected from the group consisting of propylene glycol, glycerine, polyethylene glycol, butylene glycol, and triethanolamine.

8. A method for treating a victim of a discomfort caused by topical application of capsaicin comprising the step of applying a composition comprising a carrier fluid, at least one first active ingredient comprising capsaicin, and at least one second active that functions as an analgesic ingredient to reduce capsaicin induced skin irritation topically to the skin of the victim near an area affected by the discomfort, wherein the at least one second active ingredient is selected from the group consisting of a polyol, a nettle extract, a yarrow extract, a coltsfoot extract, a birch extract, a rosemary extract, a horsetail extract, a ginger extract, a chamomile extract, a comfrey extract, a lavender extract, and a bergamot extract.

9. A method as in claim 8 wherein the composition comprises an aqueous solution of the at least one first active ingredient and the at least one second active ingredient in the carrier fluid.

10. A method as in claim 8 wherein the at least one second active ingredient is selected from the group consisting of at least one binding agent for binding capsaicin, and at least one topical analgesic agent for analgesthetizing against pain caused by the effects of capsaicin.

11. A method as in claim 9 wherein the composition contains in the range of 0.00125% to 1% by weight of capsaicin.

12. A method as in claim 9 wherein the composition contains in the range of 0.025% to 0.25% by weight of capsaicin and an amount of the at least one second active ingredient which is effective to reduce the skin irritation and pain which is caused by the capsaicin.

13. A method as in claim 12 wherein the victim suffers from the discomfort caused by musculo-skeletal pains.

14. A method as in claim 12 wherein the victim suffers from the discomfort caused by pruritis.

15. A method as in claim 8 wherein the composition comprises an oil-based solution of the at least one first active ingredient and the at least one second active ingredient in the carrier.

16. A method for making a composition useful for topical application to treat a discomfort, said method comprising mixing a carrier with at least one first active ingredient comprising capsaicin and at least one second active ingredient to reduce capsaicin induced skin irritation to form an aqueous solution containing in the range of 0.025 to 0.25 percent by weight of capsaicin, wherein the second active ingredient forms an analgesic and is selected from the group consisting of a nettle extract, a yarrow extract, a coltsfoot extract, a birch extract, a rosemary extract, a horsetail extract, a ginger extract, a chamomile extract, a comfrey extract, a lavender extract, and a bergamot extract.

17. A composition as in claim 1 comprising in the range of 0.25% to 1.0% by weight of capsaicin.

18. A composition as in claim 1 comprising in the range of 1.0% to 5% by weight of capsaicin.

19. A method as in claim 12 wherein the at least one second active ingredient is selected from the group consisting of a polyol, a lavender extract, a bergamot extract, a rosemary extract, a ginger extract, a chamomile extract, a comfrey extract, a coltsfoot extract, a nettle extract, a yarrow extract, and a birch extract.

20. A method as in claim 12 wherein the at least one second active ingredient is selected from the group consisting of a polyol, a lavender extract, a bergamot extract, a rosemary extract, a ginger extract, a chamomile extract, a comfrey extract, a coltsfoot extract, a nettle extract, and a yarrow extract.

21. A method as in claim 12 wherein the at least one second active ingredient is selected from the group consisting of a polyol, a lavender extract, a bergamot extract, a rosemary extract, a ginger extract, a chamomile extract, a comfrey extract, a coltsfoot extract, and a nettle extract.

22. A method, as in claim 12 wherein the at least one second active ingredient is selected from the group consisting of a polyol, a lavender extract, a bergamot extract, a rosemary extract, a ginger extract, a chamomile extract, a comfrey extract, and a coltsfoot extract.

23. A method as in claim 12 wherein the at least one second active ingredient is selected from the group consisting of a polyol, a lavender extract, a bergamot extract, a rosemary extract, a ginger extract, a chamomile extract, and a comfrey extract.

24. A method as in claim 12 wherein the at least one second active ingredient is selected tom the group consisting of a polyol, a lavender extract, a bergamot extract, a rosemary extract, a ginger extract, and a chamomile extract.

25. A method as in claim 12 wherein the at least one second active ingredient is selected from the group consisting of a polyol, a lavender extract, a bergamot extract, a rosemary extract, and a ginger extract.

26. A method as in claim 12 wherein the at least one second active ingredient is selected from the group consisting of a polyol, a lavender extract, a bergamot extract, and a rosemary extract.

27. A method as in claim 12 wherein the at least one second active ingredient is selected from the group consisting of a polyol, a lavender extract, and a bergamot extract.

28. A method as in claim 12 wherein the at least one second active ingredient is selected from the group consisting of a polyol, and a lavender extract.

29. A method as in claim 12 wherein the at least one second active ingredient is selected from the group consisting of a polyol, a bergamot extract, a rosemary extract, a ginger extract, a chamomile extract, a comfrey extract, a coltsfoot extract, a nettle extract, a yarrow extract, and a birch extract.

30. A method as in claim 12 wherein the at least one second active ingredient is selected from the group consisting of a polyol, a bergamot extract, a rosemary extract, a ginger extract, a chamomile extract, a comfrey extract, a coltsfoot extract, a nettle extract, and a yarrow extract.

31. A method as in claim 12 wherein the at least one second active ingredient is selected from the group consisting of a polyol, a bergamot extract, a rosemary extract, a ginger extract, a chamomile extract, a comfrey extract, a coltsfoot extract, and a nettle extract.

32. A method as in claim 12 wherein the at least one second active ingredient is selected from the group consisting of a polyol, a bergamot extract, a rosemary extract, a ginger extract, a chamomile extract, a comfrey extract, and a coltsfoot extract.

33. A method as in claim 12 wherein the at least one second active ingredient is selected from the group consisting of a polyol, a bergamot extract, a rosemary extract, a ginger extract, a chamomile extract, and a comfrey extract.

34. A method as in claim 12 wherein the at least one second active ingredient is selected from the group consisting of a polyol, a bergamot extract, a rosemary extract, a ginger extract, and a chamomile extract.

35. A method as in claim 12 wherein the at least one second active ingredient is selected from the group consisting of a polyol, a bergamot extract, a rosemary extract, and a ginger extract.

36. A method as in claim 12 wherein the at least one second active ingredient is selected from the group consisting of a polyol, a bergamot extract, and a rosemary extract.

37. A method as in claim 12 wherein the at least one second active ingredient is selected from the group consisting of a polyol, a bergamot extract.

38. A method as in claim 12 wherein the at least one second active ingredient is selected from the group consisting of a polyol, a lavender extract, a rosemary extract, a ginger extract, a chamomile extract, a comfrey extract, a coltsfoot extract, a nettle extract, a yarrow extract, and a birch extract.

39. A method as in claim 12 wherein the at least one second active ingredient is selected from the group consisting of a polyol, a lavender extract, a rosemary extract, a ginger extract, a chamomile extract, a comfrey extract, a coltsfoot extract, a nettle extract, and a yarrow extract.

40. A method as in claim 12 wherein the at least one second active ingredient is selected from the group consisting of a polyol, a lavender extract, a rosemary extract, a ginger extract, a chamomile extract, a comfrey extract, a coltsfoot extract, and a nettle extract.

41. A method as in claim 12 wherein the at least one second active ingredient is selected from the group consisting of a polyol, a lavender extract, a rosemary extract, a ginger extract, a chamomile extract, a comfrey extract, and a coltsfoot extract.

42. A method as in claim 12 wherein the at least one second active ingredient is selected from the group consisting of a polyol, a lavender extract, a rosemary extract, a ginger extract, a chamomile extract, and a comfrey extract.

43. A method as in claim 12 wherein the at least one second active ingredient is selected from the group consisting of a polyol, a lavender extract, a rosemary extract, a ginger extract, and a chamomile extract.

44. A method as in claim 12 wherein the at least one second active ingredient is selected from the group consisting of a polyol, a lavender extract, a rosemary extract, and a ginger extract.

45. A method as in claim 12 wherein the at least one second active ingredient is selected from the group consisting of a polyol, a lavender extract, and a rosemary extract.

46. A composition as in claim 1 comprising in the range of 5.0% to 99.95% by weight of capsaicin.

47. A composition as in claim 3 wherein the carrier is an oil-based fluid.

48. A composition as in claim 47 further comprising a thickening agent to provide the composition with the consistency selected from the group consisting of liniment, cream, gel, and ointment.

49. A composition as in claim 48 comprising at least one binding agent for binding capsaicin as a second active ingredient.

50. A composition as in claim 3 wherein the carrier is a solid.

51. A composition as in claim 50 further comprising a thickening agent to provide the composition with the consistency selected from the group consisting of wax and paraffin.

52. A method as in claim 8 wherein the composition comprises a solid of the at least one first active ingredient and the at least one second active ingredient in the carrier.

* * * * *